(12) United States Patent
Smith et al.

(10) Patent No.: US 7,235,261 B2
(45) Date of Patent: Jun. 26, 2007

(54) CONTROLLED RELEASE ENCAPSULATION

(75) Inventors: Leslie C. Smith, Princeton, NJ (US);
Steven G. Mushock, Highlands, NJ (US); Keith J. McDermott, Bound Brook, NJ (US)

(73) Assignee: Haarmann & Reimer Corporation, Teterboro, NJ (US)

( * ) Notice: Subject to any disclaimer, the term of this patent is extended or adjusted under 35 U.S.C. 154(b) by 0 days.

(21) Appl. No.: 10/184,285

(22) Filed: Jun. 27, 2002

(65) Prior Publication Data

US 2004/0001891 A1     Jan. 1, 2004

(51) Int. Cl.
*A61K 9/16* (2006.01)
*A61K 9/50* (2006.01)
*A61K 8/00* (2006.01)

(52) U.S. Cl. .............. 424/493; 424/490; 424/494; 424/495; 424/496; 424/497; 424/65

(58) Field of Classification Search ............ 424/65–68, 424/490, 493–497
See application file for complete search history.

(56) References Cited

U.S. PATENT DOCUMENTS

| | | | |
|---|---|---|---|
| 3,397,065 A | 8/1968 | Cunningham et al. | 99/90 |
| 3,920,849 A | 11/1975 | Marmo et al. | 426/3 |
| 4,428,869 A | 1/1984 | Munteanu et al. | 252/522 |
| 4,446,032 A | 5/1984 | Munteanu et al. | 252/8.6 |
| 4,755,397 A * | 7/1988 | Eden et al. | 427/213.3 |
| 5,176,903 A | 1/1993 | Goldberg et al. | 424/66 |
| 5,876,755 A | 3/1999 | Perring et al. | 424/489 |
| 6,063,365 A * | 5/2000 | Shefer et al. | 424/65 |

OTHER PUBLICATIONS

CRC Critical Review Journal in Food Technology, Jul. 1971, pp. 245-265, Leslie L. Balassa and Gene O. Fanger, "Microencapsulation in the Food Industry".
Soap and Chemical Specialties, Dec. 1966, pp. 67 and 155, Paul J. Barreto, "Perfumes For Specialties".
Batelle Technical Review, vol. 16, No. 2, (month unavailable) 1967, pp. 2-8, James E. Flinn and Herman Nack, "Advances in Microencapsulation Techniques".
Soap and San Chem, Jan. 1985, pp. 135, 136,137, 139, 141 and 145, Robert T. Maleeny, "Spray Dried Perfumes".
Food Flavoring, Avi Pub. Co. (month unavailable) 1960, Merory, "Spray Dried Flavors", pp. 274-277.

* cited by examiner

*Primary Examiner*—Shengjun Wang
(74) *Attorney, Agent, or Firm*—Akerman Senterfitt; Stephan A. Pendorf

(57) ABSTRACT

This invention relates to a controlled release encapsulated dry powder that is formed by an emulsion comprising: A) a fully hydrolyzed polymer, B) a hydrophobic silica, C) a modified corn starch, and D) at least one fragrance oil, which is emulsified in water and spray dried to evaporate the water obtaining the encapsulated dry powder. This invention also relates to a process for the preparation of a controlled release encapsulated dry powder that is formed by an emulsion, which is spray dried. The controlled release encapsulated dry powder is used in deodorant and antiperspirant applications.

10 Claims, No Drawings

CONTROLLED RELEASE ENCAPSULATION

FIELD OF THE INVENTION

This invention relates to a controlled release encapsulated dry powder that is formed by an emulsion comprising: A) a fully hydrolyzed polymer, B) a hydrophobic silica, C) a modified corn starch, D) at least one fragrance oil, and E) water, which is spray dried to evaporate the water obtaining the encapsulated dry powder. This invention also relates to a process for the preparation of a controlled release encapsulated dry powder that is formed by an emulsion, which is spray dried. The controlled release encapsulated dry powder is used in deodorant and antiperspirant applications.

BACKGROUND OF THE INVENTION

Deodorants are preparations, which have antimicrobial activity and which mask, remove, or decrease perspiration odor. Antiperspirants are substances, which have astringent action and inhibit the flow of perspiration. The antiperspirant/deodorant compositions may be in the form of a solid stick, an aerosol, a pump spray, a roll-on, cream, lotion, or powder. A conventional solid stick generally comprises a wax base into which the antiperspirant salts are incorporated. Roll-ons and lotions are liquid based with various possible liquids serving as the vehicle. Silicones, glycols, emollients, and etc., represent some of the suitable vehicles. A number of nonessential constituents such as suspending agents, drying agents and emollients may be added to enhance cosmetic effects.

In antiperspirant creams, the vehicle is a cream. Generally, creams contain oils and light waxes to provide the cream effect. It may also be desired to add nonessential but desirable constituents such as suspending agents, silicones, alcohol, whitening agents, and so forth. Antiperspirant powders are obviously powder based. The vehicle comprises powder constituents such as talc, kaolin, and other similar powder constituents. Other antiperspirant types include pads and gels.

Microencapsulation technology is well known in the art and is generally directed to encapsulating core materials that require protection until time of use in a protective covering. More recently, microcapsules have been developed which are "time release". U.S. Pat. No. 5,176,903 describes the time release microcapsules, which release their core materials at a controlled rate. The result is that the core material has a longer effective life since it is not immediately released from the protective microcapsule. The benefits of controlled release are obvious. For example, when pharmaceuticals are in the controlled release format, it generally allows the user to ingest or apply one long acting dose of drug instead of being obliged to ingest many small doses throughout a time period.

The encapsulation of fragrances is well known in the art. Fragrance capsules are often found in scratch and sniff inserts in magazines, in perfumes, deodorants, and a host of other applications. An antiperspirant/deodorant containing microcapsules is disclosed in U.S. Pat. No. 5,176,903 where a fragrance oil and ester are encapsulated by a food starch and polysaccharide composition.

U.S. Pat. No. 5,876,755 discloses a composition comprising a substance encapsulated within a water-sensitive matrix (PVA and starch mixtures) so as to be releasable upon contact with water or aqueous solutions, mixed with particles of inorganic carrier material (silica) carrying a poorly water-soluble oil (perfume or fragrance), such that the composition is stable at high relative humidity. However, this mixing with silica occurs after encapsulation. Typically, a water releasable encapsulate is charged into a suitable mixer such as a ribbon mixer or a tumble mixer and fumed silica containing poorly water-soluble oil is added and mixed to obtain a homogeneous powder. If a second inorganic carrier containing poorly water-soluble oil is to be used it may be added to the mixer before addition of the fumed silica and mixing is also continued to obtain a homogeneous powder. It is desirable to develop an encapsulated dry powder for use in deodorant applications that can be produced by spray drying one emulsion without post-drying mixing or treatment.

Other systems have been described which contain starch encapsulates and also contain silicas as structuring agents in the product. These include U.S. Pat. No. 3,397,065 where an edible oil is thickened with silica. Also, encapsulated flavor has been added to chewing gum, using silica as a structuring aid (U.S. Pat. No. 3,920,849). Encapsulated fragrances have been added to fabric softeners and colognes which contained silicas as suspending agent (U.S. Pat. No. 4,446,032, U.S. Pat. No. 4,428,869). However, in these systems, the silica and starch particles are not brought into intimate contact and no interaction between the particles is disclosed. Also, no perfume or flavor ingredients were adsorbed or absorbed onto the silica particles during processing.

In the spray drying process, particles are produced by a three step operation comprising (1) forming an emulsion of the liquid core material in a solution, usually aqueous, of the normally solid coating material and (2) breaking up the emulsion into droplets of desired size, e.g., in a spray nozzle, from a spinning disc, or apertured centrifugal atomizer, and (3) removing moisture in a drying environment to solidify the coating material in the droplets to form solid particles. The drying environment may be hot drying air, e.g., in a spray drying tower, a dehydrating liquid, e.g., propylene glycol; a bed of dehydrating powder, e.g., dry starch powder; or the like. The particles produced by this process, while they may be of various sizes and shapes and may be "hollow" or "solid", are characterized by cellular structure comprising many dispersed globules of the core material in a matrix of the coating material. "Solid" in this context means that a particle has more or less uniform structure throughout, as opposed to the "hollow" form of particle which has a shell surrounding a void, but it does not imply absence of pores or cells in the body thereof. Particles or capsules produced by this method have been used commercially in many applications, including foods where the core material is a flavoring oil and cosmetics where the core material is a fragrance oil. Cf. Balassa, Microencapsulation in the Food Industry, CRC Critical Review Journal in Food Technology, July 1971, pp 245–265; Barreto, Spray Dried Perfumes for Specialties, Soap and Chemical Specialties, December 1966; Maleeny, Spray Dried Perfumes, Soap and San Chem, January 1958, pp 135 et seq.; Flinn and Nack, Advances in Microencapsulation Techniques, Batelle Technical Review, Vo. 16, No. 2, pp 2–8 (1967); Merory, Food Flavorings, Avi Pub. Co. (1960), pp 274–277.

One of the known processes for producing microcapsules involves spraying into a drying atmosphere globules or droplets of an emulsion or solution containing, in a continuous aqueous phase, a hydrophilic colloid such as dextrin or gum Arabic as the coating material, with the addition if necessary of an emulsifier, and a volatile or non-volatile core material of organic liquid, hereafter sometimes referred to as oil or oils, in a dispersed phase. The products of this process are dry, somewhat porous powders containing roughly spherical, convoluted particles with the coating material in the solid state and with the organic liquid either dispersed as minute droplets throughout the particle, or dissolved in a solid matrix, or both, depending on the compatibility of the oil and coating material.

In the conventional spray drying process of producing capsules, the surface of the sprayed globule of the emulsion dries to form a solid outer crust almost immediately on contact with the drying atmosphere.

It was, therefore, an object of the present invention to prepare a controlled release encapsulated dry powder by a simplified spray drying process with components blended into one emulsion to arrive at a powder that requires no additional processing after spray drying and exhibits desirable solubility properties for use in a deodorant or antiperspirant.

SUMMARY OF THE INVENTION

This invention relates to a controlled release encapsulated dry powder comprising:
- A) from 1 to 20% by weight, based on 100% by weight of the dry powder, of at least one fully hydrolyzed polymer;
- B) from 0.025 to 2% by weight, based on 100% by weight of the dry powder, of a hydrophobic silica;
- C) from 10 to 35% by weight, based on 100% by weight of the dry powder, of a modified corn starch; and
- D) from 30 to 50% by weight, based on 100% by weight of the dry powder, of at least one fragrance oil;

which is emulsified in water and spray dried to evaporate the water obtaining the encapsulated dry powder. This invention also relates to a process for the preparation of a controlled release encapsulated dry powder that is formed by an emulsion, which is spray dried. The controlled release encapsulated dry powder is used in deodorant and antiperspirant applications.

DETAILED DESCRIPTION OF THE INVENTION

The fully hydrolyzed polymer A) is a polymer that is over 98% hydrolyzed and has a molecular weight of about 5,000 to 100,000. Polyvinyl alcohol (PVA) with a molecular weight of about 16,000 to 61,000 is preferred. More than one fully hydrolyzed polymer can be employed. The fully hydrolyzed polymer comprises 1–20% of the dry powder by weight, preferably 5–10% of the dry powder by weight.

The silica, silicon dioxide, component of the emulsion, can be any hydrophobic silica B). Fumed silica, with a colloidal structure, is made by the combustion of silicon tetrachloride in hydrogen-oxygen furnaces. The surface of a hydrophobic silica B) is modified with silicone to give excellent water repelling properties. Fumed silica hydrophobized with dimethylsilyl or trimethysilyl groups is preferred in the emulsion of the present invention. The silica component B) comprises 0.025–2% of the dry powder by weight, preferably 0.5%–1.25% by weight.

The modified corn starch C) of the emulsion comprises 10–70%, preferably 40–50%, of the dry powder by weight. Modified corn starch is a water-soluble polymer derived by acetylation, chlorination, acid hydrolysis, or enzymatic action. Modified corn starch is a polysaccharide made synthetically which usually forms colloidal solutions.

The oils are characterized by being insoluble but dispersible (emulsifiable) in water and are volatile under drying conditions which include elevated temperature and low relative humidity in the air stream. The volatile oils that can be encapsulated effectively by the present invention are fragrance oils D) such as citrus (orange, lemon, lime, and the like), spice oils (cascia, clove, wintergreen and the like), mint oils (spearmint, peppermint, and the like), woody oils (vetiver, patchouli, and the like), and mixtures thereof; perfume oils and individual components thereof, such as linalool, methyl salicylate, limonene, menthol, decanol, diethyl phthalate, carvone, citral, and mixtures thereof. The fragrance oil D) typically has a water solubility of less than 10%, preferably less than 5%, most preferably less than 1%. The fragrance oil D) contains 30–50% of the dry powder by weight, preferably 40–50% by weight.

The fragrance oils or ingredients according to the present invention can be found, for example, in S. Arctander, Perfume and Flavor Materials, Vols. I and II, Monclair, N. N., 1969, Selbstverlag or K. Bauer, D. Garbe and H. Surburg, Common Fragrances and Flavor Materials, $3^{rd}$ Ed., Wiley-VCH, Weinheim 1997.

The following are examples of fragrance ingredients: extracts from natural raw materials such as essential oils, concretes, absolutes, resins, resinoids, balsams, tinctures such as for example, ambergris tincture; amyris oil; angelica seed oil; angelica root oil; aniseed oil; valerian oil; basil oil; tree moss absolute; bay oil; armoise oil; benzoe resinoid; bergamot oil; beeswax absolute; birch tar oil; bitter almond oil; savory oil; buchu leaf oil; cabreuva oil; cade oil; calamus oil; camphor oil; cananga oil; cardamom oil; cascarilla oil; cassia oil; cassie absolute; castoreum absolute; cedar leaf oil; cedar wood oil; cistus oil; citronella oil; lemon oil; copaiba balsam; copaiba balsam oil; coriander oil; costus root oil; cumin oil; cypress oil; davana oil; dill weed oil; dill seed oil; eau de brouts absolute; oakmoss absolute; elemi oil; estragon oil; eucalyptus citriodora oil; eucalyptus oil (cineole type); fennel oil; fir needle oil; galbanum oil; galbanum resin; geranium oil; grapefruit oil; guaiacwood oil; gurjun balsam; gurjun balsam oil; helichrysum absolute; helichrysum oil; ginger oil; iris root absolute; iris root oil; jasmine absolute; calamus oil; blue camomile oil; Roman camomile oil; carrot seed oil; cascarilla oil; pine needle oil; spearmint oil; caraway oil; labdanum oil; labdanum absolute; labdanum resin; lavandin absolute; lavandin oil; lavender absolute; lavender oil; lemon-grass oil; lovage oil; lime oil distilled; lime oil expressed; linaloe oil; Litsea cubeba oil; laurel leaf oil; mace oil; marjoram oil; mandarin oil; massoi (bark) oil; mimosa absolute; ambrette seed oil; musk tincture; clary sage oil; nutmeg oil; myrrh absolute; myrrh oil; myrtle oil; clove leaf oil; clove bud oil; neroli oil; olibanum absolute; olibanum oil; opopanax oil; orange flower absolute; orange oil; origanum oil; palmarosa oil; patchouli oil; perilla oil; Peru balsam oil; parsley leaf oil; parsley seed oil; petitgrain oil; peppermint oil; pepper oil; pimento oil; pine oil; pennyroyal oil; rose absolute; rosewood oil; rose oil; rosemary oil; Dalmatian sage oil; Spanish sage oil; sandalwood oil; celery seed oil; spike-lavender oil; star anise oil; storax oil; tagetes oil; fir needle oil; tea tree oil; turpentine oil; thyme oil; Tolu balsam; tonka bean absolute; tuberose absolute; vanilla extract; violet leaf absolute; verbena oil; vetiver oil; juniperberry oil; wine lees oil; wormwood oil; wintergreen oil; ylang-ylang oil; hyssop oil; civet absolute; cinnamon leaf oil; cinnamon bark oil; and fractions thereof or ingredients isolated therefrom;

Individual fragrances from the group comprising hydrocarbons, such as for example, 3-carene; α-pinene; β-pinene; α-terpinene; γ-terpinene; p-cymene; bisabolene; camphene;

caryophyllene; cedrene; farnesene; limonene; longifolene; myrcene; ocimene; valencene; (E,Z)-1,3,5-undecatriene; styrene; diphenylmethane;

aliphatic alcohols, such as for example, hexanol; octanol; 3-octanol; 2,6-dimethylheptanol; 2-methyl-2-heptanol, 2-methyl-2-octanol; (E)-2-hexenol; (E)- and (Z)-3-hexenol; 1-octen-3-ol; a mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol; aliphatic aldehydes and their acetals such as for example, hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-5,9-undecadienal; heptanal-diethylacetal; 1,1-dimethoxy-2,2,5-trimethyl-4-hexene; citronellyl oxyacetaldehyde;

aliphatic ketones and oximes thereof, such as for example, 2-heptanone; 2-octanone; 3-octanone; 2-nonanone; 5-methyl-3-heptanone; 5-methyl-3-heptanone oxime; 2,4,4,7-tetramethyl-6-octen-3-one; aliphatic sulfur-containing compounds, such as for example, 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol; aliphatic nitriles, such as for example, 2-nonenenitrile; 2-tridecenenitrile; 2,12-tridecenenitrile; 3,7-dimethyl-2,6-octadienenitrile; 3,7-dimethyl-6-octenenitrile;

aliphatic carboxylic acids and esters thereof, such as for example, (E)- and (Z)-3-hexenylformate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexylbutyrate; (E)- and (Z)-3-hexenyl isobutyrate; hexyl crotonate; ethylisovalerate; ethyl-2-methyl pentanoate; ethyl hexanoate; allyl hexanoate; ethyl heptanoate; allyl heptanoate; ethyl octanoate; ethyl-(E,Z)-2,4-decadienoate; methyl-2-octinate; methyl-2-noninate; allyl-2-isoamyl oxyacetate; methyl-3,7-dimethyl-2,6-octadienoate;

acyclic terpene alcohols, such as for example, citronellol; geraniol; nerol; linalool; lavandulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol 2,6-dimethyl-2,5,7-octatrien-1-ol; as well as formates, acetates, propionates, isobutyrates, butyrates, isovalerates, pentanoates, hexanoates, crotonates, tiglinates and 3-methyl-2-butenoates thereof;

acyclic terpene aldehydes and ketones, such as, for example, geranial; neral; citronellal; 7-hydroxy-3,7-dimethyloctanal; 7-methoxy-3,7-dimethyloctanal; 2,6,10-trimethyl-9-undecenal; α-sinensal; β-sinensal; geranylacetone; as well as the dimethyl- and diethylacetals of geranial, neral and 7-hydroxy-3,7-dimethyloctanal;

cyclic terpene alcohols, such as for example, menthol; isopulegol; alpha-terpineol; terpinen-4-ol; menthan-8-ol; menthan-1-ol; menthan-7-ol; borneol; isoborneol; linalool oxide; nopol; cedrol; ambrinol; vetiverol; guaiol; and the formates, acetates, propionates, isobutyrates, butyrates, isovalerates, pentanoates, hexanoates, crotonates, tiglinates and 3-methyl-2-butenoates of alpha-terpineol; terpinen-4-ol; methan-8-ol; methan-1-ol; methan-7-ol; borneol; isoborneol; linalool oxide; nopol; cedrol; ambrinol; vetiverol; guaiol;

cyclic terpene aldehydes and ketones, such as, for example, menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethylionone; alpha-irone; alpha-damascone; beta-damascone; beta-damascenone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4a-methanonaphthalen-8(5H)-one; nootkatone; dihydronootkatone; acetylated cedarwood oil (cedryl methyl ketone);

cyclic alcohols, such as, for example, 4-tert.-butylcyclohexanol; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

cycloaliphatic alcohols, such as, for example, alpha,3,3-trimethylcyclo-hexylmethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

cyclic and cycloaliphatic ethers, such as, for example, cineole; cedryl methyl ether; cyclododecyl methyl ether; (ethoxymethoxy)cyclododecane; alpha-cedrene epoxide; 3a,6,6,9a-tetramethyldodecahydronaphtho[2,1-b]furan; 3a-ethyl-6,6,9a-trimethyldodecahydronaphtho[2,1-b]furan; 1,5,9-trimethyl-13-oxabicyclo[10.1.0]-trideca-4,8-diene; rose oxide; 2-(2,4-dimethyl-3-cyclohexen-1-yl)-5-methyl-5-(1-methylpropyl)-1,3-dioxan;

cyclic ketones, such as, for example, 4-tert.-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert.-pentylcyclohexanone; 5-cyclohexadecen-1-one; 6,7-dihydro-1,1,2,3,3-pentamethyl-4(5H)-indanone; 5-cyclohexadecen-1-one; 8-cyclohexadecen-1-one; 9-cycloheptadecen-1-one; cyclopentadecanone;

cycloaliphatic aldehydes, such as, for example, 2,4-dimethyl-3-cyclohexene carbaldehyde; 2-methyl-4-(2,2,6-trimethyl-cyclohexen-1-yl)-2-butenal; 4-(4-hydroxy-4-methylpentyl)-3-cyclohexene carbaldehyde; 4-(4-methyl-3-penten-1-yl)-3-cyclohexene carbaldehyde;

cycloaliphatic ketones, such as, for example, 1-(3,3-dimethylcyclohexyl)-4-penten-1-one; 1-(5,5-dimethyl-1-cyclohexen-1-yl)-4-penten-1-one; 2,3,8,8-tetramethyl-1,2,3,4,5,6,7,8-octahydro-2-naphtalenyl methyl ketone; methyl-2,6,10-trimethyl-2,5,9-cyclododecatrienyl ketone; tert.-butyl-(2,4-dimethyl-3-cyclohexen-1-yl)ketone;

esters of cyclic alcohols, such as, for example, 2-tert.-butylcyclohexyl acetate; 4-tert.-butylcyclohexyl acetate; 2-tert.-pentylcyclohexyl acetate; 4-tert.-pentylcyclohexyl acetate; decahydro-2-naphthyl acetate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5 or 6-indenyl acetate; 4,7-methano-3a,4,5,6,7,7a-hexahydro-5 or 6-indenyl propionate; 4,7-methano-3a,4,5,6,7,7a-hexahydro-5 or 6-indenyl-isobutyrate; 4;7-methanooctahydro-5 or 6-indenyl acetate;

esters of cycloaliphatic carboxylic acids, such as, for example, allyl 3-cyclohexyl-propionate; allyl cyclohexyl oxyacetate; methyl dihydrojasmonate; methyl jasmonate; methyl 2-hexyl-3-oxocyclopentanecarboxylate; ethyl 2-ethyl-6,6-dimethyl-2-cyclohexenecarboxylate; ethyl 2,3, 6,6-tetramethyl-2-cyclohexenecarboxylate; ethyl 2-methyl-1,3-dioxolane-2-acetate;

araliphatic alcohols, such as, for example, benzyl alcohol; 1-phenylethyl alcohol; 2-phenylethyl alcohol; 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

esters of araliphatic alcohols and aliphatic carboxylic acids, such as, for example, benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzyl acetate; alpha,alpha-dimethylphenylethyl acetate; alpha,alpha-dimethylphenylethyl butyrate; cinnamyl acetate; 2-phenoxyethyl isobutyrate; 4-methoxybenzyl acetate; araliphatic ethers, such as for example, 2-phenylethyl methyl ether; 2-phenylethyl isoamyl ether; 2-phenylethyl-1-ethoxyethyl ether; phenylacetaldehyde dimethyl acetal; phenylacetaldehyde diethyl acetal; hydratropaaldehyde dimethyl acetal; phenylacetaldehyde glycerol acetal; 2,4,6-trimethyl-4-phenyl-1,3-dioxane; 4,4a, 5,9b-tetrahydroindeno[1,2-d]-m-dioxin; 4,4a,5,9b-tetrahydro-2,4-dimethylindeno[1,2-d]-m-dioxin;

aromatic and araliphatic aldehydes, such as, for example, benzaldehyde; phenylacetaldehyde; 3-phenylpropanal; hydratropaldehyde; 4-methylbenzaldehyde; 4-methylphenylacetaldehyde; 3-(4-ethylphenyl)-2,2-dimethylpropanal; 2-methyl-3-(4-isopropylphenyl)propanal; 2-methyl-3-(4-tert.-butylphenyl)propanal; 3-(4-tert.-butylphenyl)propanal; cinnamaldehyde; alpha-butylcinnamaldehyde; alpha-amylcinnamaldehyde; alpha-hexylcinnamaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylene-dioxybenzaldehyde; 3,4-dimethoxybenzaldehyde; 2-methyl-3-(4-methoxy-phenyl)propanal; 2-methyl-3-(4-methylendioxyphenyl)propanal;

aromatic and araliphatic ketones, such as, for example, acetophenone; 4-methylacetophenone; 4-methoxyacetophenone; 4-tert.-butyl-2,6-dimethylacetophenone; 4-phenyl-2-butanone; 4-(4-hydroxyphenyl)-2-butanone; 1-(2-naphthalenyl)ethanone; benzophenone; 1,1,2,3,3,6-hexamethyl-5-indanyl methyl ketone; 6-tert.-butyl-1,1-dimethyl-4-indanyl methyl ketone; 1-[2,3-dihydro-1,1,2,6-tetramethyl-3-(1-methyl-ethyl)-1H-5-indenyl]ethanone; 5',6',7',8'-tetrahydro-3', 5',5',6',8',8'-hexamethyl-2-acetonaphthone;

aromatic and araliphatic carboxylic acids and esters thereof, such as, for example, benzoic acid; phenylacetic acid; methyl benzoate; ethyl benzoate; hexyl benzoate; benzyl benzoate; methyl phenylacetate; ethyl phenylacetate; geranyl phenylacetate; phenylethyl phenylacetate; methyl cinnamate; ethyl cinnamate; benzyl cinnamate; phenylethyl cinnamate; cinnamyl cinnamate; allyl phenoxyacetate; methyl salicylate; isoamyl salicylate; hexyl salicylate; cyclohexyl salicylate; cis-3-hexenyl salicylate; benzyl salicylate; phenylethyl salicylate; methyl 2,4-dihydroxy-3,6-dimethylbenzoate; ethyl 3-phenylglycidate; ethyl 3-methyl-3-phenylglycidate;

nitrogen-containing aromatic compounds, such as, for example, 2,4,6-trinitro-1,3-dimethyl-5-tert.-butylbenzene; 3,5-dinitro-2,6-dimethyl-4-tert.-butylacetophenone; cinnamonitrile; 5-phenyl-3-methyl-2-pentenonitrile; 5-phenyl-3-methylpentanonitrile; methyl anthranilate; methy-N-methylanthranilate; Schiff's bases of methyl anthranilate with 7-hydroxy-3,7-dimethyloctanal, 2-methyl-3-(4-tert.-butylphenyl)propanal or 2,4-dimethyl-3-cyclohexene carbaldehyde; 6-isopropylquinoline; 6-isobutylquinoline; 6-sec.-butylquinoline; indole; skatole; 2-methoxy-3-isopropylpyrazine; 2-isobutyl-3-methoxypyrazine;

phenols, phenyl ethers and phenyl esters, such as, for example, estragole; anethole; eugenol; eugenyl methyl ether; isoeugenol; isoeugenol methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresyl phenylacetate;

heterocyclic compounds, such as, for example, 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

lactones, such as, for example, 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 1,15-pentadecanolide; cis- and trans-11-pentadecen-1,15-olide; cis- and trans-12-pentadecen-1, 15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene-1,12-dodecanedioate; ethylene-1,13-tridecanedioate; coumarin; 2,3-dihydrocoumarin; octahydrocoumarin.

It may be desirable to add an appropriate amount of water to emulsify the oil and spray dry the emulsion. It may also be desirable to add small amounts of other constituents such as additives including flow agents, system stabilizers, chelating agents, and anti-oxidants, and so forth to the emulsion.

The emulsion used to prepare the dry powder of the present invention is prepared by combining two mixtures prepared separately. Mixture 1 is obtained by adding the fully hydrolyzed polymer to water at about 80–100° C. The two components are mixed until the fully hydrolyzed polymer is dissolved in the water. Once the solution is homogeneous and cools to roughly 40–50° C., the modified corn starch is added. This solution of 3 components is mixed with moderate agitation for about 30 minutes and then the refractive index is checked. After another 15 minutes, the refractive index is checked again and compared to the first reading. Mixing continues until two consecutive readings that are 15 minutes apart are similar to each other.

Mixture 2 is prepared by adding the hydrophobic silica to the fragrance oil. Because the silica is not soluble in the oil, these two form a suspension, which is mixed until homogeneous.

Mixture 2 is then added to Mixture 1 to form the emulsion. The two mixtures are emulsified at a high shear with a suitable homogenizer until the oil droplet size is 3 microns or less. The homogenizer must have the capacity to efficiently form a stable emulsion at various volumes. The emulsion thus obtained is then spray-dried using conventional spray drying techniques.

To accomplish moisture removal by spray drying, any suitable spray drying tower may be employed. Typically, spray drying towers comprise an upper cylindrical portion where the emulsion to be dried is introduced by rotating discs, nozzles, and the like, and a lower conical portion leading to the product outlet at the bottom of the cone. The drying medium, usually heated air, may be introduced at the top with the emulsion to be dried, the so-called cocurrent type, or adjacent to the bottom, the so-called countercurrent type. In general, for products of the invention in the form of very fine powders, it is preferred to use the cocurrent system with centrifugal separation of product from the air after the product has been removed at the bottom of the conical portion of the spray tower. The air used in the drying process is ordinarily taken from the atmosphere and passed over heated surfaces before being introduced into the drying tower. These surfaces may be heated electrically, by flame, by steam, or the like, in accordance with the usual techniques, which are understood by those skilled in the spray drying art. Ordinarily, the air at the time it is introduced in the tower will have a temperature between about 160° C. to 220° C.

A heated air chamber type spray dryer with a particle separator is more preferred. The emulsion is preferably introduced through a rotating disk called a centrifugal atomized wheel with atomization capabilities. The preferred change in temperature is about 100° C. between the inlet and outlet temperature. The emulsions of the present invention are preferably subjected to temperatures below 100° C. during the drying process, the outlet temperature. The heated inlet air is thus approximately 100 degrees above the desired outlet air. The emulsion water content determines pump speed; the evaporative cooling of the water to be removed determines the outlet temperature.

The prepared emulsion is delivered to the preheated, stabilized dryer with a pump. The pump must be able to deliver various volumes of emulsions with varying viscosities. The pump feed rate is adjusted to maintain the established parameters. A flow agent is added to the finished product before sieving. Sieving equipment is used to remove large, misshaped, and agglomerated particles from the finished product.

The dry powder of the spray drying process contains microcapsules of the fragrance oil from 5–500 microns. Preferably the microcapsules of the invention are of a smaller diameter, namely 10–250 microns, for maximal effectiveness.

The dry powder obtained from the spray-dried emulsion is particularly useful in deodorant and antiperspirant applications. The fragrance oil encapsulated in the dried powder exhibits excellent controlled release properties. The dry powder does not immediately dissolve upon contact with water and therefore is suitable in deodorant and antiperspirant compositions. Microcapsules of the present invention take 8 to 40 times longer to dissolve compared to encapsulated fragrances with modified corn starch.

The microcapsules of the invention may be incorporated into any antiperspirant/deodorant known in the art. Generally a cosmetically effective amount of microcapsules ranges from 0.01–10.0%, with 0.1–5.0% preferred, and 0.5–5.0% most preferred.

The following examples further illustrate details for the preparation and use of the compositions of the present invention. The present invention, which is set forth in the foregoing disclosure, is not to be limited either in spirit or scope by these examples. Those skilled in the art will readily understand that known variations of the conditions and processes of the following preparative procedures can be used to prepare these compositions.

Unless otherwise noted, all temperatures are degrees Celsius and all percentages are percentages by weight in the dry powder.

EXAMPLES

Example 1

The following spray dried powder was prepared from an emulsion made with a polyvinyl alcohol Mowiol 3–98 commercially available from. Clariant Corporation; fumed silica (HiCap 100 Starch commercially available from National Starch), AEROSIL® R972 available from Degussa, modified corn starch, the fragrance oil 807414F, commercially available from HAARMANN & REIMER, with a water solubility of less than 5% and the anti-oxidant BHT. See Table 1 for the compositions of the emulsion and the dry powder.

The emulsion was prepared in accordance with the invention. Mixtures 1 and 2 were prepared separately. Mixture 1 was formed by 1) adding the PVA to 90° C. water, 2) mixing homogeneously, 3) cooling to 45° C., 4) adding modified corn starch and 5) mixing until the refractive index was stable. Mixture 2 was prepared by adding the silica to the fragrance oil creating a suspension. The two mixtures were combined and emulsified to obtain a droplet size of less than 3.0 microns. A commercial duty one (1) gallon waring blender was used as the homogenizer. The emulsion was spray dried through a centrifuged atomizer in a spray drying tower with an inlet temperature of 190° C. and an outlet temperature of 90° C. 400 grams of dry powder resulted from 900 grams of emulsion.

TABLE 1

| Component | weight % in the emulsion | weight % in the powder |
|---|---|---|
| Polyvinyl alcohol | 5.00 | 9.89 |
| Fumed Silica | 0.50 | 0.99 |
| Modified starch | 20.00 | 39.58 |
| Fragrance | 24.99 | 49.45 |
| Anti-oxidants | 0.045 | 0.09 |
| Water | 49.465 | |
| Total | 100 | 100 |

Example 2

Other spray dried powders were formed as in Example 1 with the same processing conditions and the same components, but with varying ranges. The resulting compositions of the dry powders are represented in Table 2.

TABLE 2

| Component | Powder 1 Weight % | Powder 2 Weight % | Powder 3 Weight % |
|---|---|---|---|
| Modified Corn Starch | 40 | 50 | 45 |
| Polyvinyl alcohol | 10 | 10 | 5 |
| Fumed Silica | 1 | 1 | 1 |
| Fragrance Oil | 49 | 39 | 49 |

Example 3

The dried powder (Powder 1) of Example 2 and a spray-dried powder containing 50% modified corn starch and 50% fragrance oil were dissolved in water to demonstrate the controlled released properties of the spray-dried powders. The spray-dried powder containing 50% modified corn starch and 50% fragrance oil dissolved after only 20 seconds. The dried powder of Example 2, however, dissolved in water over a 12 minute period. This Example was carried out on a microscopic slide in order to observe the microcapsules dissolve.

Example 4

Deodorant Stick Formulation

In a suitable vessel, dipropylene glycol, propylene glycol, deionized water, triclosan and sodium stearate were combined and heated to 75° C. while mixing. The mixed components were allowed to cool while still being mixed. The Polycap™ and Fragrance were added while mixing. The mixture was then poured into a suitable container and allowed to cool.

TABLE 3

| Ingredients | Wt. % |
| --- | --- |
| Dipropylene glycol | 54.25 |
| Propylene glycol | 25.00 |
| Deionized Water | 10.00 |
| Triclosan | 0.25 |
| Sodium Stearate | 8.00 |
| PolyCap ™ (HAARMANN & REIMER) | 1.50 |
| Fragrance (HAARMANN & REIMER) | 1.00 |
| TOTAL | 100.00 |

Deodorant sticks prepared according to Table 3 were compared to control sticks without the Polycap™ component. The overall results showed that the fragrance encapsulated in the Polycap™ dry powder was reduced in its olfactive intensity when applied to the underarm, compared to the fragrance not encapsulated in the control sticks. The Polycap™ fragrance also lasted longer than in the control stick. Sticks were aged at 45° C. for 1 month and the Polycap™ particles were found to still be intact and still provided the above-mentioned performance.

Example 5

Antiperspirant Solid Formulation

In a suitable vessel, cyclomethicone, hydrogenated polydecane, polyethylene, hydrogenated castor oil, PPG-3, PEG-8 and stearyl alcohol were combined and heated to 75° C. while mixing. The components were mixed until the waxes became molted and homogeneous, wherein the mixture is allowed to cool to 70° C. while mixing. Aluminum zirconium, silica, the fragrance and the Polycap™ were added to the mixture while mixing until dispersed. The mixture was allowed to cool with mixing to a temperature of 65° C. Finally, the resulting mixture is poured into suitable containers.

TABLE 4

| Ingredients | Wt. % |
| --- | --- |
| Aluminum Zirconium (Tetrachlorohydrox Gly Reach AZP –908 SUF) (Reheis) | 22.000 |
| VS-7158 Cyclomethicone (GE Silicones) | 23.500 |
| Silkflo 364-NF Hydrogenated Polydecane (Lipo Chemicals) | 20.000 |
| AC-617 Polyethylene (Allied Signal) | 3.000 |
| Castorwax NF Hydrogenated Castor Oil (CasChem) | 2.000 |
| PPG-3-Myrisyl Ether Promyristul PM-3 (Croda) | 8.000 |
| PEG-8 Distearate Protamate 400-DS (Protameen Chemicals) | 3.000 |
| Stearyl Alcohol (Lanette 18 by Henkel Corporation) | 15.000 |
| Cab-O-Sil M-5 Silica (Cabot Corporation) | 1.000 |
| Fragrance (HAARMANN & REIMER) | Up to 1.0% |
| Polycap (HAARMANN & REIMER) | Up to 1.5% |
| TOTAL | 100.000 |

Antiperspirant sticks were prepared using the procedure in Table 4. A control stick was also prepared without the PolyCap™. The overall results showed that the fragrance encapsulate, in the PolyCap™ dry powder was reduced in its olfactive intensity when applied to the underarm compared to the control stick. The fragrance from the PolyCap™ stick also lasted longer in the underarm compared to the control stick.

Sticks were aged at 45° C. for one (1) month and the PolyCap™ particles were found to be intact and still provided the above-mentioned performance.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A controlled release dry powder comprising:
    A) from 1 to 20% by weight, based on 100% by weight of the dry powder, of a poly vinyl alcohol, wherein the poly vinyl alcohol is over 98% hydrolyzed and has a molecular weight of about 5,000 to 100,000;
    B) from 0.025 to 2% by weight, based on 100% by weight of the dry powder, of a hydrophobic silica;
    C) from 20 to 70% by weight, based on 100% by weight of the dry powder, of a modified corn starch; and
    D) from 30 to 50% by weight, based on 100% by weight of the dry powder, of at least one fragrance oil
    which is emulsified in water and spray dried to evaporate said water obtaining said dry powder.

2. The dry powder according to claim 1 that is formed from said emulsion that further comprises anti-oxidants.

3. The dry powder according to claim 1 wherein said emulsion comprises 5 to 10% by weight of the emulsion, of the poly vinyl alcohol.

4. The dry powder according to claim 1 wherein said silica is fumed hydrophobic silica.

5. The dry powder according to claim 1 wherein said emulsion comprises 0.5% to 1.25% by weight of the dry powder, of the hydrophobic silica.

6. The dry powder according to claim 1 wherein said fragrance oil has a water solubility less of than 10%.

7. The dry powder according to claim 6 wherein said fragrance oil has a water solubility less of than 1%.

8. The dry powder according to claim 1 wherein said dry powder comprises 40–50% by weight of the dry powder, of the fragrance oil.

9. An antiperspirant comprising a controlled release dry powder comprising:
  A) from ito 20% by weight, based on 100% by weight of the dry powder, of a poly vinyl alcohol, wherein the poly vinyl alcohol is over 98% hydrolyzed and has a molecular weight of about 5,000 to 100,000;
  B) from 0.025 to 2% by weight, based on 100% by weight of the dry powder, of a hydrophobic silica;
  C) from 20 to 70% by weight, based on 100% by weight of the dry powder, of a modified corn starch; and
  D) at least one fragrance oil
  which is emulsified in water and spray dried to evaporate said water obtaining said dry powder.

10. A deodorant stick comprising a controlled release dry powder comprising:
  A) from 1 to 20% by weight, based on 100% by weight of the dry powder, of a poly vinyl alcohol, wherein the poly vinyl alcohol is over 98% hydrolyzed and has a molecular weight of about 5,000 to 100,000;
  B) from 0.025 to 2% by weight, based on 100% by weight of the dry powder, of a hydrophobic silica;
  C) from 20 to 70% by weight, based on 100% by weight of the dry powder, of a modified corn starch; and
  D) at least one fragrance oil
  which is emulsified in water and spray dried to evaporate said water obtaining said dry powder.

* * * * *